United States Patent [19]

Guirguis

[11] Patent Number: 5,024,238
[45] Date of Patent: Jun. 18, 1991

[54] BLOOD WITHDRAWING APPARATUS AND ANTIGEN TESTING METHOD
[75] Inventor: Raouf A. Guirguis, Rockville, Md.
[73] Assignee: Cancer Diagnostics, Inc., Rockville, Md.
[21] Appl. No.: 408,547
[22] Filed: Sep. 18, 1989

Related U.S. Application Data
[63] Continuation-in-part of Ser. No. 308,763, Jan. 10, 1989.
[51] Int. Cl.⁵ ................................................. A61B 5/00
[52] U.S. Cl. ..................................... 128/771; 604/404
[58] Field of Search ....................... 128/760, 762, 771; 604/318, 404; 422/56, 60

[56] References Cited
U.S. PATENT DOCUMENTS

| | | | |
|---|---|---|---|
| 3,777,739 | 12/1973 | Raitto | 128/2 |
| 3,881,465 | 5/1975 | Raitto | 128/2 |
| 3,894,845 | 7/1975 | McDonald | 128/762 |
| 3,958,561 | 5/1976 | Bucalo | 128/762 |
| 4,040,791 | 8/1977 | Kuntz | 23/259 |
| 4,042,337 | 8/1977 | Griffith | 23/259 |
| 4,084,937 | 4/1978 | Beach | 23/259 |
| 4,244,920 | 1/1981 | Manschot et al. | 422/102 |
| 4,473,530 | 9/1984 | Villa-Real | 422/58 |
| 4,492,258 | 1/1985 | Lichtenstein et al. | 141/1 |
| 4,557,274 | 12/1985 | Cawood | 128/760 |
| 4,573,983 | 3/1986 | Annia | 604/322 |
| 4,700,714 | 10/1987 | Fuisz | 128/767 |
| 4,741,346 | 5/1988 | Wong et al. | 128/760 |
| 4,879,098 | 11/1989 | Oberhardt et al. | 128/760 |

Primary Examiner—Max Hindenburg
Attorney, Agent, or Firm—Gipple & Hale

[57] ABSTRACT

An apparatus for testing biological molecular indicators in blood comprising a tubular container, and a sample compartmentalized container holding labelled ligands and beads with immobilized ligands. Blood is collected in the tubular container under pressure to flow through the sample compartmentalized container which screens off the red blood cells so that enzymes of the labelled ligands are carried by the blood fluid to a reactant solution which is colored by specific labelled ligands to indicate the presence of specific ligands.

17 Claims, 6 Drawing Sheets

BLOOD WITHDRAWING APPARATUS AND ANTIGEN TESTING METHOD

RELATED CASES

This application is a continuation-in-part application of U.S. patent application Ser. No. 07/308,763 filed Jan. 10, 1989, pending.

BACKGROUND OF THE INVENTION

The present invention is directed to medical and laboratory fluid specimen collecting and testing apparatus, and more specifically to an apparatus for detecting the presence of specific antigens in biological fluids.

The family of immunoassay works upon the simple principle that is the specific recognition of an antigen by an antibody. Thus specific antigen detection and quantification requires an antibody which recognizes the uniqueness of an antigen. The antigen binding site of antibodies recognizes about six amino acids or their equivalent in mass. One unique binding site serves as an identifying marker for that protein.

When a definitive antibody for a given antigen is available it is used to identify the antigen in the sample mixture. Once the antibody combines with the antigen a means is needed to recognize the complex.

The present invention is directed toward apparatus which can use immunoassay in sample treatment apparatus for diagnostic and testing purposes.

It is generally necessary in diagnosing and testing for many diseases to collect biological fluids from a patient, e.g., sputum, blood, pleural and peritoneal cavity fluids, urine, etc. for analysis. It is important during the collection handling of biological fluid specimens that the potential of specimen contamination and the spread of any infection from the specimen be minimized. In addition there is also the potential for specimen damage during the collection and/or shipment process as well as the potential for destruction of certain components of the specimen because the packaging does not screen fluids or causes mixing of different fluid components which will negate the test results or result in false data being obtained when the specimen is tested.

There currently exists a need to collect and test biological fluids for the presence of cancer which can be quickly and easily accomplished through color testing.

A typical specimen collecting apparatus is shown by U.S. Pat. No. 4,741,346. This apparatus includes a base stand which supports the specimen vial in an upright position. A funnel is inserted in the open end of the specimen vial and surrounds and encloses the upper portion of the vial. The base stand has an upwardly extending tubular wall which at least partially surrounds the vial in connection with the cap and allows the user to remove the vial without touching the surface or coming in contact with the specimen. Examples of various types of liquid containers for collecting and transporting urine are shown by U.S. Pat. Nos. 3,777,739; 3,881,465; 4,042,337; 4,084,937; 4,244,920; 4,492,258 and 4,700,714.

Another specimen collection device shown by U.S. Pat. No. 4,040,791 discloses a collection receptacle having a nipple upon which is mounted a specimen container which receives a predetermined amount of the specimen in a sealed condition. The specimen container is provided with an integrally formed cap which is placed over the opening in which the collector nipple is inserted. U.S. Pat. No. 4,557,274 discloses a midstream urine collector having a funnel which transmits urine into a cup member which is covered by a membrane cover.

A combined strip testing device and collection apparatus is shown by U.S. Pat. No. 4,473,530 and is directed to an apparatus which integrates testing and collection by having chemical reagent test strips present within the tube together with specific gravity reading means allowing immediate testing of the urine. U.S. Pat. No. 4,573,983 is directed towards a liquid collection system having an antiseptic member on the discharge section which uses a filter of air and bacteria impervious material to filter the urine.

It is therefore desirable to provide an easy to handle disposable apparatus which uses a fluid sample such as blood and captures various antigens from the blood so that cancer testing can be performed quickly and accurately with minimum time.

BRIEF SUMMARY OF THE INVENTION

The invention is directed toward a blood fluid analysis device. This device is in the form of a sterile sealed blood sample vial having an interior compartmentalized blood treatment container moveably seated in the vial. The blood treatment container has labelled primary antibody in one compartment, matching antigen covalently bound on beads in a second compartment and a sponge soaked with a color inducing solution in another compartment. A solution such as hydrogen peroxide can be placed in the vial prior to insertion of the treatment container and is separated from a sponge color solution compartment by a vacuum and optional breakable membrane. The primary antibody is provided prelabelled with the enzyme HRP (horseradish peroxidase). The blood is added to the vial through a sealed cap where it engages a treatment container with a circular (disk) membrane having a 5 micron pore size. The disk membrane provides the surface upon which red blood cells engage but cannot pass allowing blood serum which has a pH of 7.2 to pass through it into the compartment of the container. The red blood cells pile up on the surface of the membrane forming an impermeable barrier causing the membrane to act as a piston head and push the treatment container down through the vial. The serum antigen reacts with labelled antibody housed in one compartment of the treatment container to form antigen-antibody complex. If there is an absence of the antigen in the specimen sample the antibody will remain unoccupied and seek the binding site of the beads with antigen in the bead compartment. Another compartment of the treatment container holds a sponge soaked with the solution ABTS which reacts with the antibody label enzyme to produce a color. The test result indicating presence of a cancer is visualized by a color or lack of color of the solution.

It is thus an object of the invention, particularly where ligands such as antigens and antibodies are being removed from the body fluids for testing to detect and visually indicate specific antigens in the body fluid samples. Previously such testing has been accomplished by a series of tests involving a number of different containers and expensive laboratory equipment. Mass testing using such a series of tests is expensive, time consuming, and often unsatisfactory.

In the accompanying drawings, there is shown an illustrative embodiment of the invention from which these and other of objectives, novel features and advantages will be readily apparent.

DETAILED DESCRIPTION OF THE INVENTION

Figure 1:
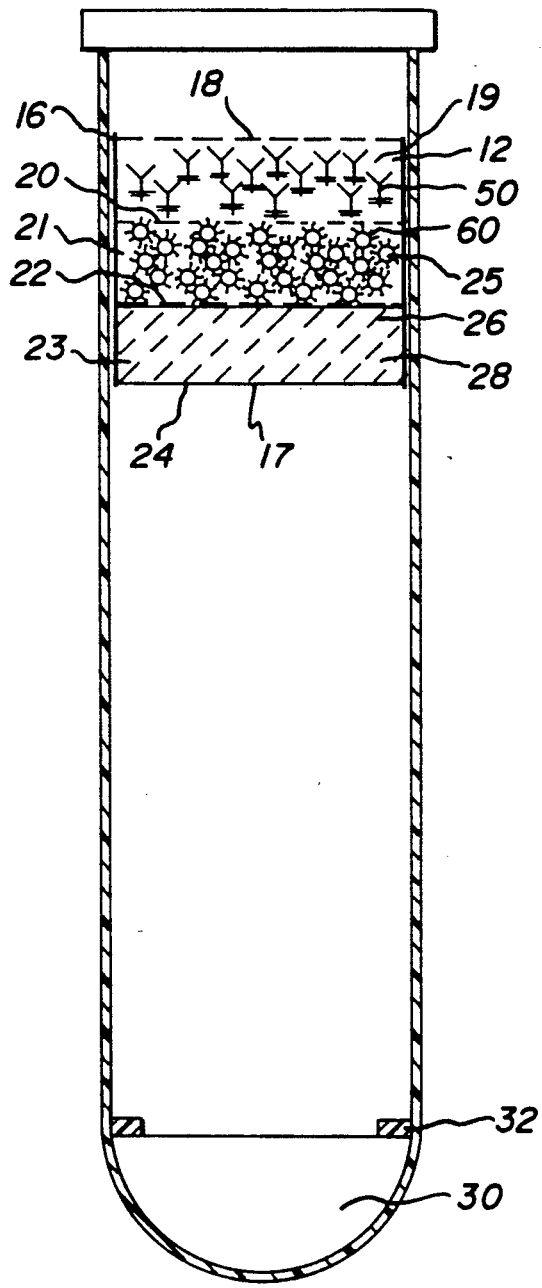
FIG. 1 is a cross sectional view of the inventive blood testing device.

The preferred embodiment and best mode of the invention is seen in FIGS. 1 through 5. The invention shown in the drawings comprises a blood sample vial 10 with sample treatment container 12 mounted therein. The sample treatment container can be moveable as shown in FIGS. 1–5 or fixed as shown in the alternate embodiment shown in FIGS. 6 and 7. While the invention can be used for any body fluid it is primarily designed for use in collecting blood samples for use in testing for the presence of various kinds of cancer in the body.

Figure 2:
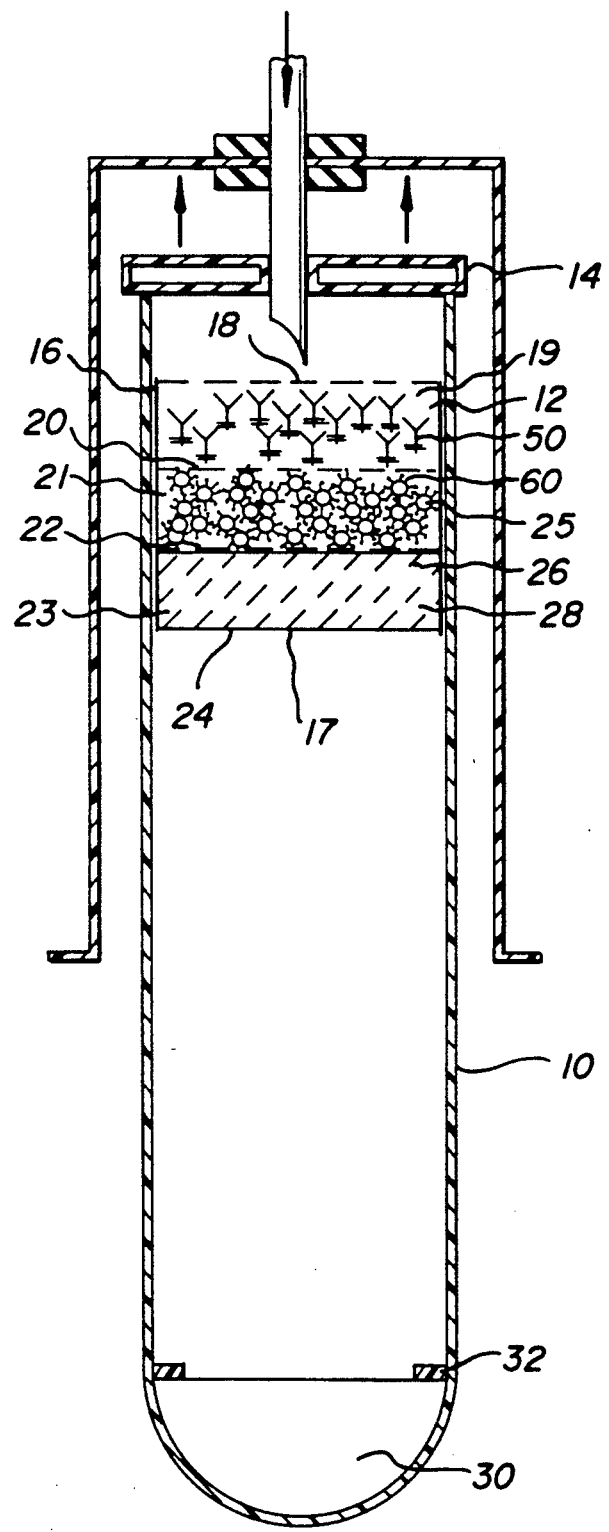
FIG. 2 is a cross sectional view of the invention of FIG. 1 showing a needle inserted through the vial seal and blood with red and white blood cells entering the vial with direction of movement of the treatment container shown by arrow A.
Figure 3:
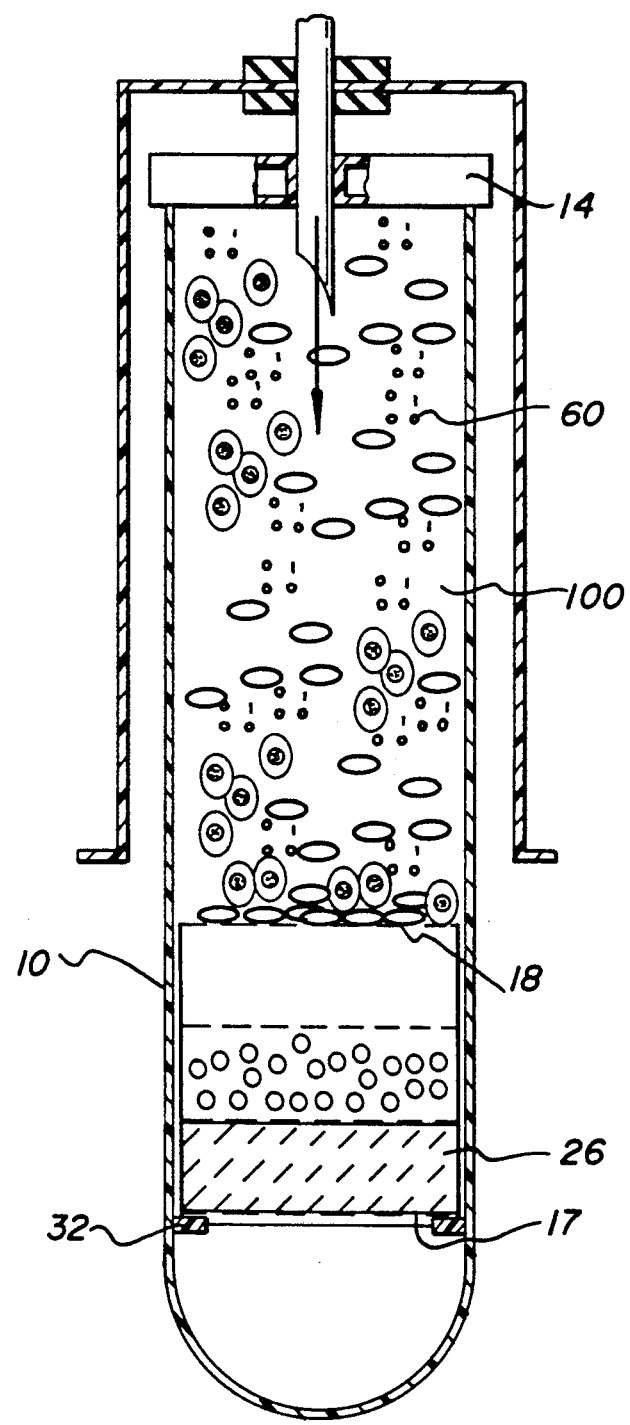
FIG. 3 is a cross sectional view of the invention of FIG. 1 showing sequential movement of the treatment container from that shown in FIG. 2 with red and white blood cells entering the vial with direction of movement shown by arrow A and the red blood cells piled upon the container membrane pushing down on the container membrane.
Figure 4:
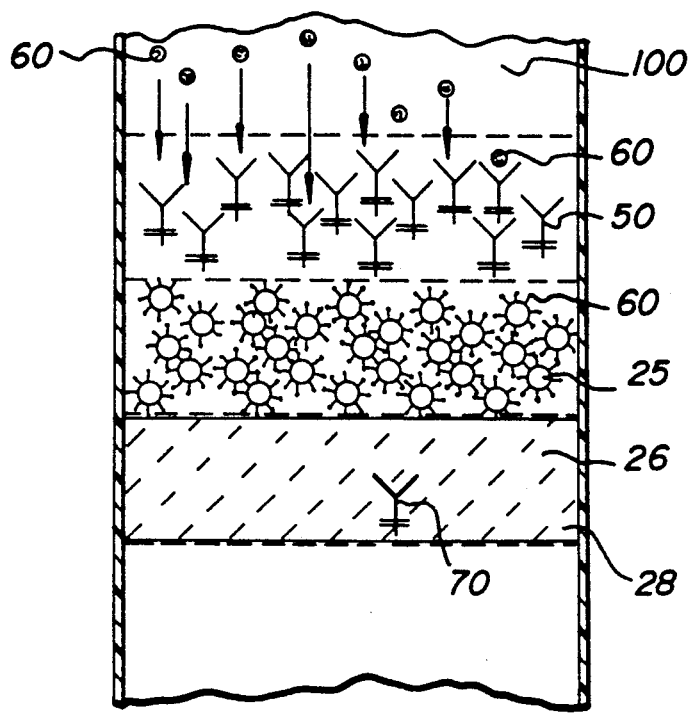
FIG. 4 is an exploded enlarged cross sectional schematic view of the antibody antigen complexing in the treatment container when a specific designated antigen is present in the blood to produce a test positive color.
Figure 5:
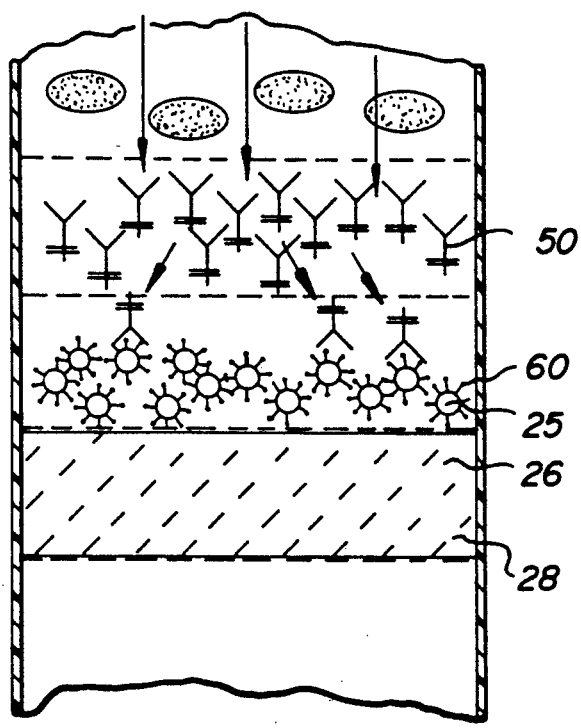
FIG. 5 is an exploded enlarged cross sectional schematic view when antigen is not present in the blood resulting in no complexing with the primary antibody causing the primary antibody to seek receptors on the immobilized antigen and not to be carried to the sponge solution to produce a test negative no color.

As shown in FIGS. 1 through 3, a blood sample vial 10 is constructed of polystyrene. This vial is provided with a rubber or plastic seal 14 and is of a standard construction with a sterile interior. One such vial which can be used with the invention is VACUTAINER, a vial manufactured by Becton Dickinson Company. A cylindrical treatment container 12, having an exterior cylindrical wall 16 with a exterior diameter which is slightly less than the interior diameter of the vial, is sectioned into three compartments by porous membrane 18 and radial wall members 20, 22 and 24. The first compartment 19 of the treatment container is defined by exterior wall 16, a membrane 18 with a pore size ranging from 0.5 to 5 microns mounted on one end of wall 16 and a porous interior radial wall member 20 mounted or secured to the interior surface of wall 16. Wall 20 and the other interior walls can be adhesively affixed to wall 16, secured by sonic welding or mounted on an interior step, rib, or channel formed on the interior surface of wall 16.

Compartment 19 contains lyophilized primary labelled antibodies 50 having a binding site contoured to the epitope structure and chemistry of antigen 60. The antibodies 50 are labelled with HRP (horseradish peroxidase), an enzyme that detoxifies hydrogen peroxide, $H_2O_2$, by converting it to water. HRP initiates this transformation when it gives hydrogen peroxide a pair of electrons. The enzyme subsequently collects these electrons from suitable donors. Thus the total color generated by peroxidase depends upon the relative rates of color generation and product inactivation of the enzyme.

The middle or interior compartment 21 is formed by cylindrical wall 16, and porous radial interior walls 20 and 22. Compartment 21 contains antigen 60 immobilized (covalently bound) on beads 25. The antigen 60 has epitopes which have a high affinity for the binding sites of the primary labelled antibody 50. The container compartment 21 may be filled with testing beads 25 of all forms and sizes which can be specifically manufactured for high affinity resin beads with specific antigens immobilized onto the solid phase resin (e.g. Actigel-ALD, Protein A, Protein G ... etc.) so that antigens in the sample can bind to their specific antibodies or alternately the antibodies can become bound while passing through the resin module and become immobilized as well. The principle of affinity chromatography requires that a successful separation of a biospecific ligand is available and that it can be chemically immobilized to a chromatographic bed material, the matrix. Numbers of methods well known in the art have been used to couple or immobilize the antigen to a variety of activated resins. Examples of immobilization techniques which exhibit variable linkage are those formed by the reaction of the reactive groups on the support with amino, thiol, hydroxyl, and carboxyl groups on the protein ligand. The selection of the ligand is influenced by two factors. First, the ligand should exhibit specific and reversible binding affinity for the substance to be purified and secondly it should have chemically modifiable groups which allow it to be attached to the matrix without destroying its binding activity.(Examples of such are Protein G Sepharose manufactured by Pharmacia, Hydrazide AvidGel Ax manufactured by BioProbe International, and Actigel-ALD manufactured by Sterogene Bioseparation Inc.)

Another advantage to the use of Actigel-ALD is that it does not cross link proteins therefore allowing proteins to retain high bioactivity after their immobilization. Actigel-ALO SUPER FLOW also available from Sterogene Bioseparation Inc. permits a linear flow rate of up to 3000 cm/h which would fit nicely with the flow rates in the apparatus (approx 10–100 cm/min).

Compartment 23 is formed by wall 16, porous radial interior wall 22 and distal porous radial end wall 24 and contains a sponge 26 preferably soaked with ABTS solution 28. In place of sponge 26 any fluid holding material could be used. A hydrogen peroxide ($H_2O_2$) solution 30 is placed in the bottom of the vial 10 when OPD or TMB or other dual substrate systems are used.

The color solution 28 used in the sponge 26 is preferably a substrate manufactured by Kirkegaard & Perry Labs under one of several acronyms namely: ABTS (2,2'-azino-di-[3-ethylbenzthiazoline sulfonate (6)]; OPD (ortho-phenylene diamine); or TMB (tetramethylkbenzidine). In choosing the substrate, the sensitivity of the immunoassay is determined by the discrimination of the antibody reagents. When this occurs, the use of a more sensitive substrate serves only to proportionately increase the signal and the background. The result is more color but the same signal-to-noise ratio. Should the more sensitive substrate push the absorbance over the cut-off of the reader, the faster substrate may in fact reduce the signal-to-noise ratio.

Figure 6:
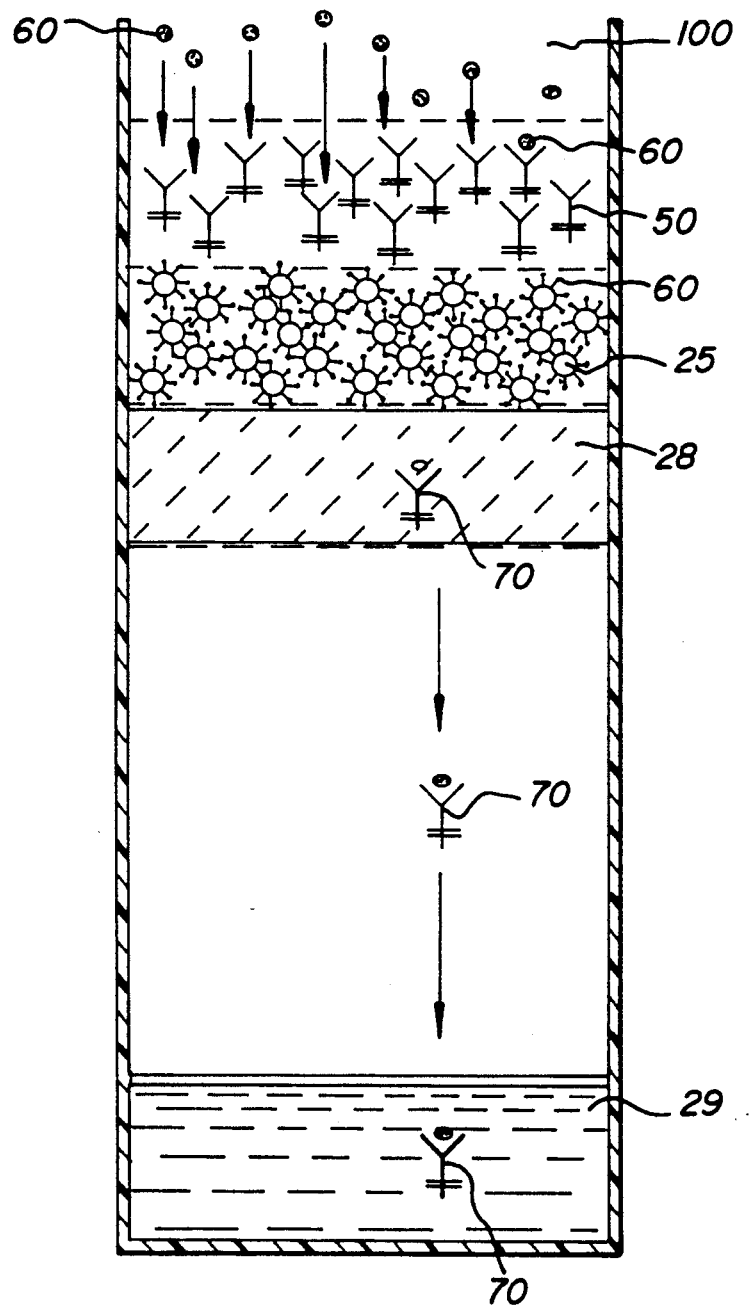
FIG. 6 is an alternate embodiment of the fixed sample treatment container correlating to FIG. 4 showing an exploded enlarged cross sectional schematic view of the antibody antigen complexing in the treatment contains when a specific designated antigen is present in the blood to produce a test positive color.
Figure 7:
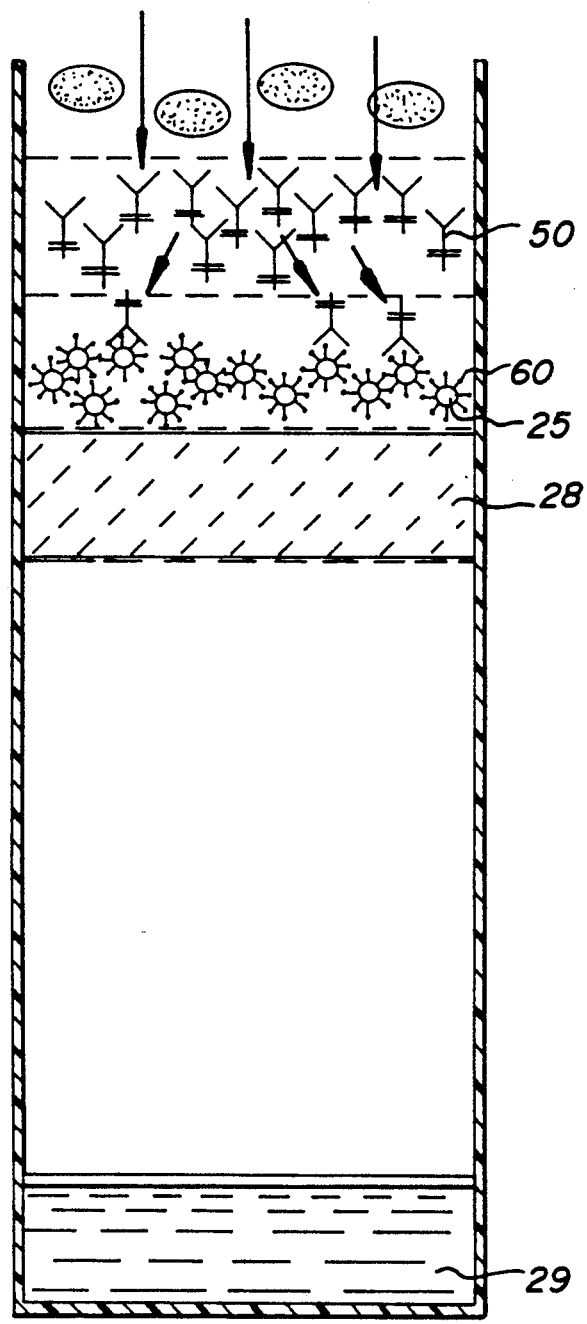
FIG. 7 is an alternate embodiment of the fixed sample treatment container correlating to FIG. 5 showing an exploded enlarged cross sectional schematic view when antigen is not present in the blood resulting in no complexing with the primary antibody causing the primary antibody to seek receptors on the immobilized antigen and not to be carried to the sponge solution to produce a test negative no color.

The preferred color solution 28 or 29 as used in the embodiment shown in FIGS. 6 and 7 of the present invention is ABTS and when this solution is used in the sponge or adsorber material 26 held in compartment 23 there is no need to add solution 30. The preferred ABTS substrate is a one-component substrate. The HRP label on the primary antibody 50 turns ABTS to a blue-green color and there is no change in color or absorbance when the reaction is stopped with SDS(sodium dodecyl sulfate). If the assay optimization indicates the sensitivity of the immunoasssay is limited by the color generated by the HRP substrate then the more sensitive TMB substrate would give more color development without a corresponding increase in the background. Another advantage of the TMB substrate is that it often lowers the amount of antibody and antigen reagents required for the immunoassay. TMB substrate is a two component liquid substrate and requires hydrogen peroxide. HRP converts TMB to a blue product. When the reaction is stopped by acidification, the TMB product becomes yellow. ODP is generally provided as a tablet that is dissolved in buffer at the time of use. HRP converts OPD to a yellow product which continues to oxidize into a brown precipitate. Upon acidification the OPD product becomes orange.

A marker stop 32 is etched or formed on the interior surface of the vial 10 and forms a stop for the end 17 of the cylindrical container wall 16 and also forms the coloration reading indicator area for the antigen presence test.

The resin bead material 25 with matrix and primary ligand (in this case immobilized antigen 60) having had flow contact with the filtered blood fluid, now in serum form, with a pH of 7.2 captures through antigen-antibody reaction or immune reaction the specific ligand component carried by the fluid namely, the no complexed primary labelled antibody 50 which was formerly contained in compartment 19. This antibody 50 as previously noted was provided prelabelled with coloring enzyme HRP. When the specific antigen 60 is present in the testing sample 100 which is added to the container, the antigen 60 reacts with the antibody 50 to form antigen-antibody complexes 70. The complexed antigen-antibody 70 passes through compartment 21 into compartment 23 where this labelling enzyme of the antibody 50 reacts with the ABTS soaked sponge 26 turning the resulting fluid into a blue green color as is clearly shown in FIG. 4. If there is an absence of the antigen in the specimen sample 100 the antibody 50 will remain unoccupied and will react with the antigen 60 immobilized on beads 25 as shown on FIG. 5. On the other hand, if the antigen is present, anitgen-antibody complexes 70 will be formed and transported to the ABTS solution in sponge 26. The degree of color developed as shown in solution 28 or solution 30 should correlate with the amount of prelabeled antibody/antigen complexes 70 which in turn correlates with the amount of antigen 60 present in the sample 100. The positive control reflects the current state of the coloring reagents as well as the prelabelled antibody at the time the test is performed.

In the foregoing description, the invention has been described with reference to a particular preferred embodiment, although it is to be understood that specific details shown are merely illustrative, and the invention may be carried out in other ways without departing from the true spirit and scope of the following claims:

What is claimed is:

1. An apparatus for testing molecular specimens in biological fluids comprising a fluid container; a specimen treatment unit mounted in said fluid container, said specimen treatment unit comprising means defining a plurality of fluid treatment compartments which allow fluid flow therethrough, a primary labelled antibody means contained in one of said fluid treatment compartments, a predetermined antigen matched to said primary labelled antibody means is covalently bound to bead means contained in another of said fluid treatment compartments, and a solution carrying means containing a reactive colorization material is contained in another of said fluid treatment compartments.

2. An apparatus for testing molecular specimens in biological fluids as claimed in claim 1 wherein said fluid container is a sealed tubular vial and is adapted to receive blood through one end, a membrane means is mounted to said specimen treatment unit to prevent flow of red blood cells through said specimen treatment unit and associated compartments and acts as a piston head upon the buildup of said red cells to drive said specimen treatment unit along said tubular container.

3. An apparatus for testing molecular specimens in biological fluids as claimed in claim 1 wherein said specimen treatment unit is moveably mounted in said fluid container.

4. An apparatus for testing molecular specimens in biological fluids as claimed in claim 1 wherein said specimen treatment unit is fixedly secured in said fluid container.

5. An apparatus for collecting molecular specimens from biological fluids and marking said molecular specimens with a color indicator for visual identification comprising a tubular container; a specimen collection unit moveably mounted in said tubular container, said specimen collection unit comprising a housing divided into a plurality of separate compartments, labelled antibody means positioned in one of said compartments and bead means with covalently bound antigen located in another of said compartments downstream from said labelled antibody means compartment; a membrane is mounted to said specimen collection unit to prevent flow of red blood cells through said fluid collection unit, said membrane acting as a piston head upon the buildup of said red blood cells to drive said specimen collection unit along said tubular container and colorization means located within said tubular container downstream from said bead means compartment adapted to react with said labelled antibody means to create a visual color indicator.

6. An apparatus as claimed in claim 5 wherein said labelled antibody means is labelled with horseradish peridase enzyme.

7. An apparatus as claimed in claim 5 wherein said specimen collection unit comprises a cylindrical housing, said housing having at least one porous end wall, a membrane means mounted to one of said ends, divider means dividing said cylindrical housing into a plurality of compartments, said divider means comprising a plurality of radial porous wall members mounted in said cylindrical housing.

8. An apparatus as claimed in claim 5 wherein said colorization means includes a coloration solution means.

9. An apparatus as claimed in claim 8 wherein said coloration solution means is ABTS.

10. An apparatus as claimed in claim 8 wherein said coloration solution means is OPD.

11. An apparatus as claimed in claim 8 wherein said coloration solution means is TMB.

12. An apparatus as claimed in claim 5 wherein said colorization means is a sponge soaked in a color reagent, said sponge being contained in one of said specimen collection unit housing compartments.

13. An apparatus as claimed in claim 12 wherein said color reagent is ABTS.

14. An apparatus as claimed in claim 5 wherein said membrane ranges from 0.2 to 0.5 microns in thickness.

15. An apparatus for collecting molecular specimens from biological fluids and marking said specimens with a color indicator for visual identification comprising a tubular container; a specimen collection unit mounted in said tubular container, said specimen collection unit comprising a housing divided into a plurality of separate compartments, labelled antibody means mounted in one of said compartments and bead means with covalently bound antigen matched to said labelled antibody means and antigens to be tested in said biological fluids located in another of said compartments downstream from said labelled antibody means compartment; a membrane mounted to said specimen collection unit to prevent flow of red blood cells through said fluid collection unit and a solution absorption means mounted in a separate compartment downstream from said bead means compartment adapted to react with said labelled antibody means to create a visual color indicator.

16. A method of testing for predetermined molecular bodies in a blood specimen comprising the steps of:
   a. collecting blood into an apparatus for collecting biological fluids comprising an elongated tubular apparatus;
   b. passing the blood through a blood treatment container comprising a cylindrical hollow piston defining a plurality of separated chambers, one of which contains a labelled antibody means, and one of which has a cover which prevents the flow of blood cells therethrough while allowing the flow of blood serum therethrough;
   c. moving the blood treatment container along the tubular apparatus by the action f the blood against collected blood cells on the cover while allowing blood serum to flow through separated compartments of the blood treatment container into the base of the tubular apparatus; and
   d. mixing color developing solution with the blood serum which has passed through at least one chamber of the treatment container to obtain a visual color test result.

17. A method of testing for predetermined molecules in blood comprising the steps of:
   a. positioning a moveable test container means into a fluid collecting apparatus, said test container means comprising a housing defining a plurality of separated chambers containing means with different biological indicators, one of which is labelled;
   b. transporting blood fluid and causing it to flow through the test container's separated chambers to transport said test container means and contact bead means with different biological indicators and carry at least one labelled biological indicator; and
   c. mixing said blood fluid and carried labelled biological indicator with a substance to chemically obtain a color or lack of color indicating a specific test result.

* * * * *